(12) United States Patent
Bossi et al.

(10) Patent No.: US 7,412,025 B1
(45) Date of Patent: Aug. 12, 2008

(54) ENERGY BEAM PULSE ECHO SYSTEM FOR IMAGING IN A STRUCTURE

(75) Inventors: Richard H. Bossi, Renton, WA (US); John L. Adamski, Kenmore, WA (US); William G. Bartholet, Issaquah, WA (US)

(73) Assignee: The Boeing Company, Chicago, IL (US)

( * ) Notice: Subject to any disclaimer, the term of this patent is extended or adjusted under 35 U.S.C. 154(b) by 38 days.

(21) Appl. No.: 11/533,504

(22) Filed: Sep. 20, 2006

(51) Int. Cl.
*G01N 23/04* (2006.01)

(52) U.S. Cl. .............................. 378/57; 378/87; 378/198

(58) Field of Classification Search .................... 378/51, 378/53, 57, 86, 87, 88, 198; 73/620
See application file for complete search history.

(56) References Cited

U.S. PATENT DOCUMENTS

2001/0021241 A1* 9/2001 Swift et al. .................... 378/57

* cited by examiner

*Primary Examiner*—Courtney Thomas
(74) *Attorney, Agent, or Firm*—Charles L. Moore; Moore & Van Allen, PLLC

(57) ABSTRACT

A system for imaging in a structure may include an energy beam source to direct an energy beam at the structure and a detector to detect a backscatter of the energy beam from any object in the structure. The system may also include a time-resolved function to generate an image of any object in the structure using the backscatter of the energy beam.

38 Claims, 4 Drawing Sheets

ENERGY BEAM PULSE ECHO SYSTEM FOR IMAGING IN A STRUCTURE

BACKGROUND OF THE INVENTION

The present invention relates to detection of objects, people or the like within a structure, and more particularly to an energy beam pulse echo system and method for imaging with a structure.

Being able to efficiently and non-intrusively image in a structure to detect objects, such as people or things, would facilitate and make safer the job for such entities as homeland security, law enforcement and the military. There is a need to be able to provide such imaging despite the nature of the structure. For example, the ability to penetrate any potential thickness of concrete or to penetrate metal structures, such as shipping containers or the like, that may block radiowave and microwave radiation. Also the ability to image in a structure to permit visualization of the interior of the structure and to determine the location of objects within the structure, such as how many rooms, the arrangement of such rooms and in what room certain objects of interest may be located, would also be highly beneficial. Also of benefit would be the ability to perform such imaging at a distance, and under some circumstances, without the conduct of such process being immediately apparent other than to those individuals using the system or method.

BRIEF SUMMARY OF THE INVENTION

In accordance with an embodiment of the present invention, a system for imaging in a structure may include an energy beam source to direct an energy beam at the structure and a detector to detect a backscatter of the energy beam from any object in the structure. The system may also include a time-resolved function to generate an image of any object in the structure using the backscatter of the energy beam.

In accordance with another embodiment of the present invention, a system for imaging in a structure may include an energy beam source to direct an energy beam at the structure and a detector to detect a backscatter of the energy beam from any object in the structure. The system may also include a time-resolved function to generate an image of any object in the structure using the backscatter of the energy beam. The system may also include at least one vehicle to move at least one of the energy beam source and the detector relative to the structure.

In accordance with another embodiment of the present invention, a method for imaging in a structure may include directing an energy beam at the structure and detecting a backscatter of the energy beam from any object in the structure. The method may also include generating an image of any object in the structure by applying a time-resolved function to the backscatter of the energy beam.

In accordance with another embodiment of the present invention, a method of imaging in a structure may include generating an energy beam to provide an energy beam pulse echo from any object in the structure. The method may also include generating an image of any object in the structure from the energy beam pulse echo.

Other aspects and features of the present invention, as defined solely by the claims, will become apparent to those ordinarily skilled in the art upon review of the following non-limited detailed description of the invention in conjunction with the accompanying figures.

DETAILED DESCRIPTION OF THE INVENTION

The following detailed description of embodiments refers to the accompanying drawings, which illustrate specific embodiments of the invention. Other embodiments having different structures and operations do not depart from the scope of the present invention.

Figure 1A:
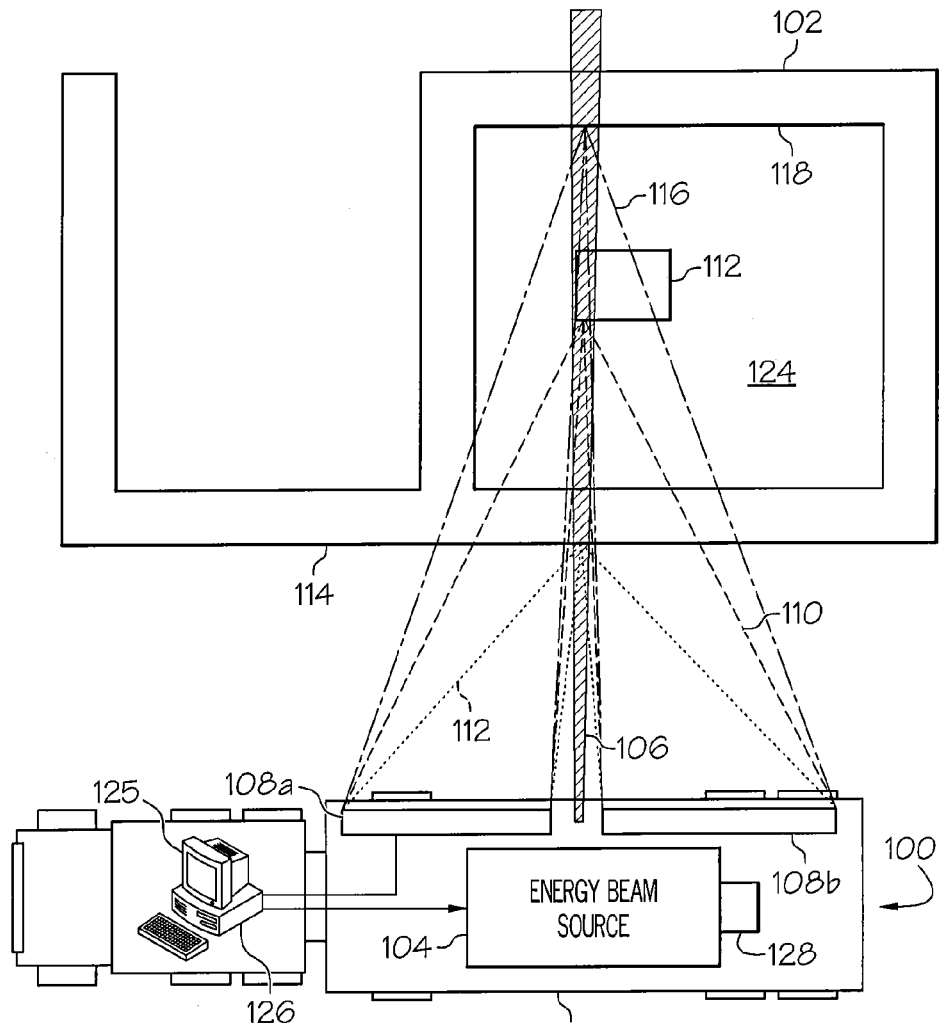
FIG. 1A is an illustration of an example of an energy beam pulse echo system for imaging in a structure in accordance with an embodiment of the present invention.

FIG. 1A is an illustration of an example of an energy beam pulse echo system 100 for imaging in a structure 102 in accordance with an embodiment of the present invention. The system 100 may include an energy beam source 104 to direct an energy beam 106 at the structure 102. The energy beam source 104 may be an X-ray source similar to that provided by MXISystem, Inc. of Nashville, Tenn. or a similar device. The energy beam source 104 may generate an energy beam of a high intensity, narrow beam of monoenergetic photons in a very short pulse or burst, on the order of a few picoseconds. For example, energy beam source 104 may generate an energy beam having characteristics of about 200 kilo electron volts (keV) to about 2000 keV, a beam pulse width of about 9-10 picoseconds or less, a divergence of less than about one degree, a repetition rate of about 10 Hertz and photons per pulse of about 1 E11.

The system 100 may also include a detector 108 to detect a backscatter 110 of the energy beam 106 from any object 112 or backscatter source in the structure 102. The detector 108 may be defined by a first portion 108a and a second portion 108b. The first detector portion 108a may be spaced from the second detector portion 108b to permit the energy beam source 104 to direct the energy beam 106 between the two detector portions 108a and 108b. The detector 108 may also detect a backscatter 112 or return of the energy beam photons from a front wall 114 of the structure 102, a backscatter 116 from a back wall 118 and a backscatter from any interior walls (not shown in FIG. 1A).

The system 100 may also include a time-resolved function 120 or process (FIG. 1B) to determine distance to the backscattering source. Combined with a transport vehicle 117 the time-resolved data can be converted into an image 122 (FIG. 1B) of any object 112 in the structure 102 using the backscatter 110 of the energy beam 106. The backscatter 112 from the front wall 114 and the backscatter 118 from the back wall 118 and any interior walls may also be presented in the image 122 using the time-resolved function 120 to present a visualization of the structure 102, an interior 124 of the structure 102 and any objects 112 in the structure 102. In this manner a substantially precise location of the object within the structure 102 and relative to parts of the structure (front wall 114, back wall 118, any interior walls, etc.) may be determined. An example of the time-resolved data for visualizing any object 112 in a structure 102 will be described with reference to FIG. 4. The image 122 may be presented to a user or system operator on a display 125 as illustrated in FIG. 2B.

Figure 1B:
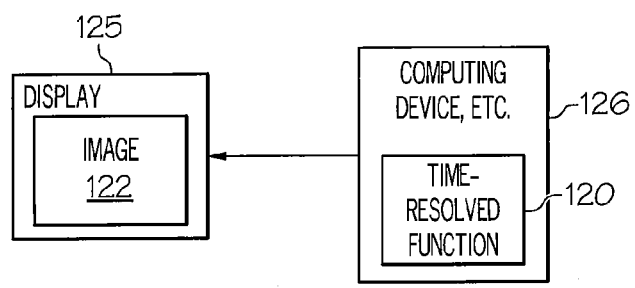
FIG. 1B is an illustration of an example of a computing device and display that may be used with the energy beam pulse echo system of FIG. 1A.

The time-resolved function 120 may be operable on a computing device 126 or similar device as illustrated in FIG. 1B. The computing device 126 and time-resolved function 120 may be defined or formed as part of the detector 108 or may be integrated as part of the detector package 108. Accordingly, the detector 108 may be described as include a time gating feature to perform the time-resolved function 120 or a similar function. The detector 108 may have a predetermined time gating sensitivity to detect the backscatter of an energy beam having a pulse duration of about 9-10 picoseconds or less. With such a short pulse or burst, photons can be detected in a time-resolved fashion by a very high speed detector gating technology. The time-resolved function 120 substantially eliminates any noise so that only a small number, about 10 to about 100 or more, photons from the initial energy beam pulse or burst need be detected to identify the object 112 in the structure 102.

As described in more detail with reference to FIG. 3, the time-resolved function 120 or time gating feature may include an element or operation to determine a spatial depth of any object 112 based on a time of return of the backscatter 110 of the energy beam 106 or return of photons of the energy beam 106. The time of return of the backscatter 110 of the energy beam 106 may include a function of a distance of the object 112 from the energy source 104. Likewise, the backscatter 112 from the front wall 114 and the back wall 118 will also be a function of the distance from the energy source 104. In this manner, the relative location of the object 112 and walls may be determined and presented in the image 122.

The system 100 may also include a vehicle 126. The vehicle 126 may be large enough to house the energy beam source 126, the detector 108 and any associated equipment. The vehicle 126 may permit the system 100 to be translated or moved relative to the structure to determine horizontal positioning for the image 122. The beam 106 may be scanned up and down vertically to complete the three dimensional coverage. The energy beam 106 may have a predetermined beam size to provide a horizontal and a vertical resolution of the object 122. In some embodiments of the present invention, the energy beam 106 may have a predetermined beam size of between about one inch and about two feet and a selected pulse duration of about twenty (20) picoseconds. An embodiment of the present invention that may use a larger beam size will be described with reference to FIG. 2. With a smaller beam size, a mechanism 128 may be provided to scan the energy beam 106 to create or provide a volumetric image 122 of the location of the object 112 within the structure 102. The energy beam 106 may be scannable in a raster mode or back and forth, or up and down action as the vehicle 126 translate the source 104 and detector 108 relative to the structure 102 to substantially cover the entire structure.

Figure 2:
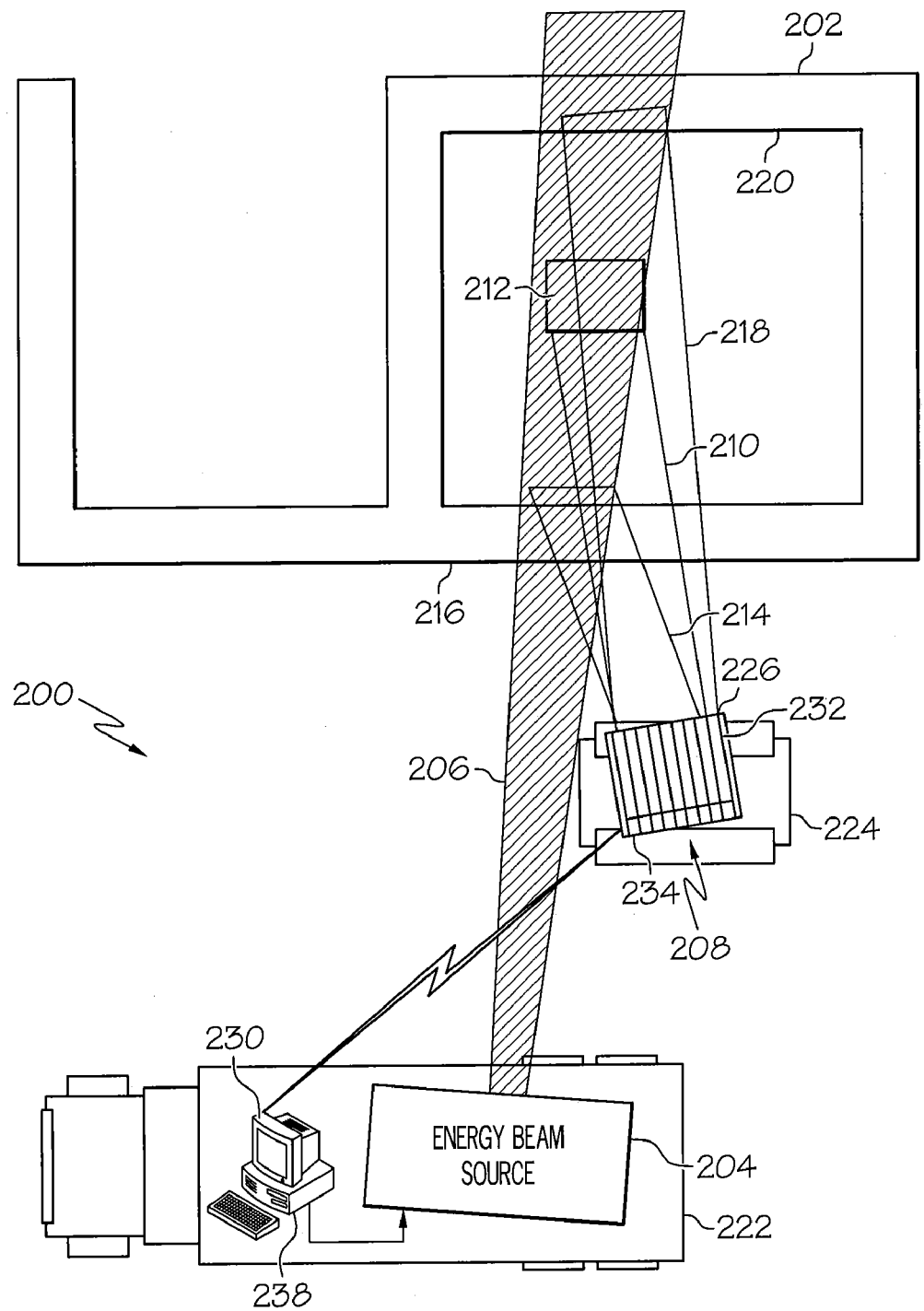
FIG. 2 is an illustration of an example of another energy beam pulse echo system for imaging in a structure in accordance with another embodiment of the present invention.

FIG. 2 is an illustration of an example of another energy beam pulse echo system 200 for imaging in a structure 202 in accordance with another embodiment of the present invention. The system 200 may include a energy beam source 204 to direct an energy beam 206 at the structure 202. The energy beam source 204 may be similar to the energy beam source 104 of FIG. 1A to generate an energy beam 206 with substantially the same characteristics as the energy beam 106 of FIG. 1A except that the size of the energy beam 206 may be substantially larger than the energy beam 106. The size of the energy beam 206 may be on the order of several feet while the size of the energy beam 106 may be on the order of a few inches. For example the energy beam 106 may have a size of about one inch and the energy beam 206 may have a size of about 4 feet or more to cover a substantial larger area of the structure 202 with an energy beam pulse.

The system may also include a detector 208 to detect a backscatter 210 of the energy beam 206 from any object 212 in the structure 202. The detector 208 may also detect backscatter 214 from a front wall 216, backscatter 218 from a back wall 220, and backscatter form any interior walls (not shown in FIG. 2).

The energy beam source 204 may be mounted to a first vehicle 222 for movement of the energy source 204 and the detector 208 may be mounted to a second, autonomous vehicle 224. The autonomous vehicle 224 may be an unmanned remotely controlled vehicle or small unmanned ground vehicle (SUGV) that may be controlled from the first vehicle 222. In this respect, the detector 208 may be moved to within close proximity to the structure 202 while the first vehicle 222, which may be manned, may located at a substantial distance from the structure 202.

The detector 208 may include a plurality of collimated detectors 226 to provide a horizontal and a vertical resolution of an image (not shown in FIG. 2) that may be presented on a display 230. The image presented on the display 230 may be similar to the image 122 of FIG. 1B. The collimated detectors 226 may include a collimator array 232 and a detector array 234. The system 200 may also include a time-resolved function to provide a depth resolution of the image of the object 212. The time-resolved function (not shown in FIG. 2) may be similar to the time-resolved function 120 described with reference to FIG. 1B. The time-resolved function may be operable on a computing device 238 or similar device. The time-resolved function may also define a time gating function that may be part of the detector 226 similar to that described with respect to detector 108 of FIG. 1A. The display 230 and computing device 238 may be similar to the display 125 and computing device 126 of FIGS. 1A and 1B.

Figure 3:
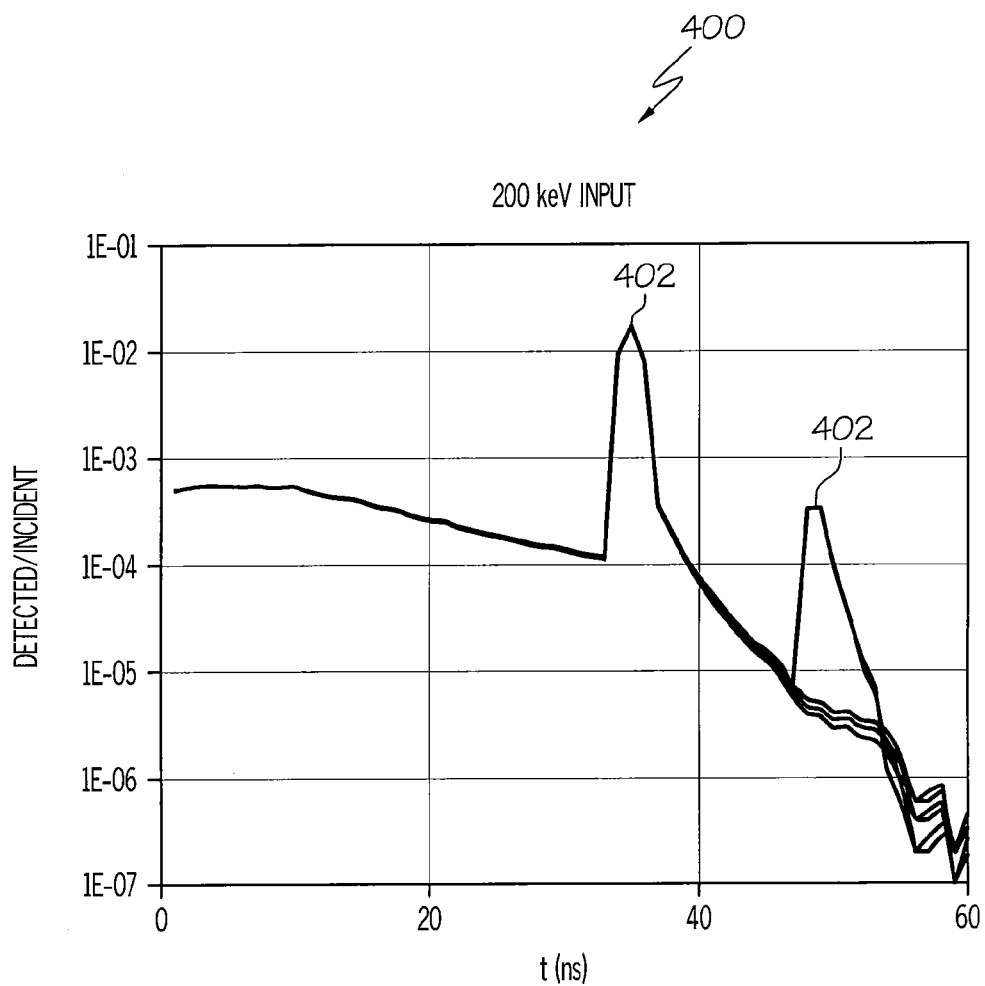
FIG. 3 is a flow chart of an example of a method for imaging in a structure in accordance with an embodiment of the present invention.

FIG. 3 is a flow chart of an example of a method 300 for imaging in a structure in accordance with an embodiment of the present invention. The method 300 may be embodied in the system 100 of FIG. 1A or system 200 of FIG. 2. In block 302, an energy beam or energy beams may be directed on a structure, such as a building, a vehicle, a container or other structure. The energy beam may include a multiplicity of monoenergetic photons of a predetermined beam size. The energy beam may also have a selected pulse or burst duration. The energy beam may have characteristics similar to energy beam 106 or 206 of FIGS. 1 and 2, respectively.

In block 304, a backscatter of the energy beam or return of the energy beam photons may be detected to identify any objects within the structure. Any objects may be detected or identified using a time-resolved function or method similar to that previously described to determine a spatial depth of a scatter source or object in the structure. The time-resolved function may involve a detector or detectors with a predetermined gating sensitivity, speed detector gating technology or the like to determine the spatial depth of the object relative to a burst or pulse duration of the original energy beam. The backscatter or scatter return may be a function of the distance of the object from the energy beam source.

In block 306, a vertical and a horizontal resolution of any object or scatter source may be based on a beam size or may be determined by a collimated detector scheme. In block 308, the energy beam may be scanned to create or provide a backscatter volumetric image of a location of the object in the structure. This is similar to the embodiment of the present invention described with reference to FIGS. 1A and 1B. In another embodiment of the present invention a larger beam size may be directed at any location of the structure to identify any object within the structure. This is similar to the embodiment of the present invention described with reference to FIG. 2. Similar to that previously discussed, the beam size may be larger as the beam 206 in FIG. 2 to cover more of any object 212 and the collimated detector scheme of the detector 208 may provide the vertical and horizontal resolution of the image. The energy beam 106 in FIG. 1A may be substantial smaller to cover a smaller area of the object 112. The energy beam 106 may be scanned to provide the vertical and horizontal resolution of the image.

Figure 4:
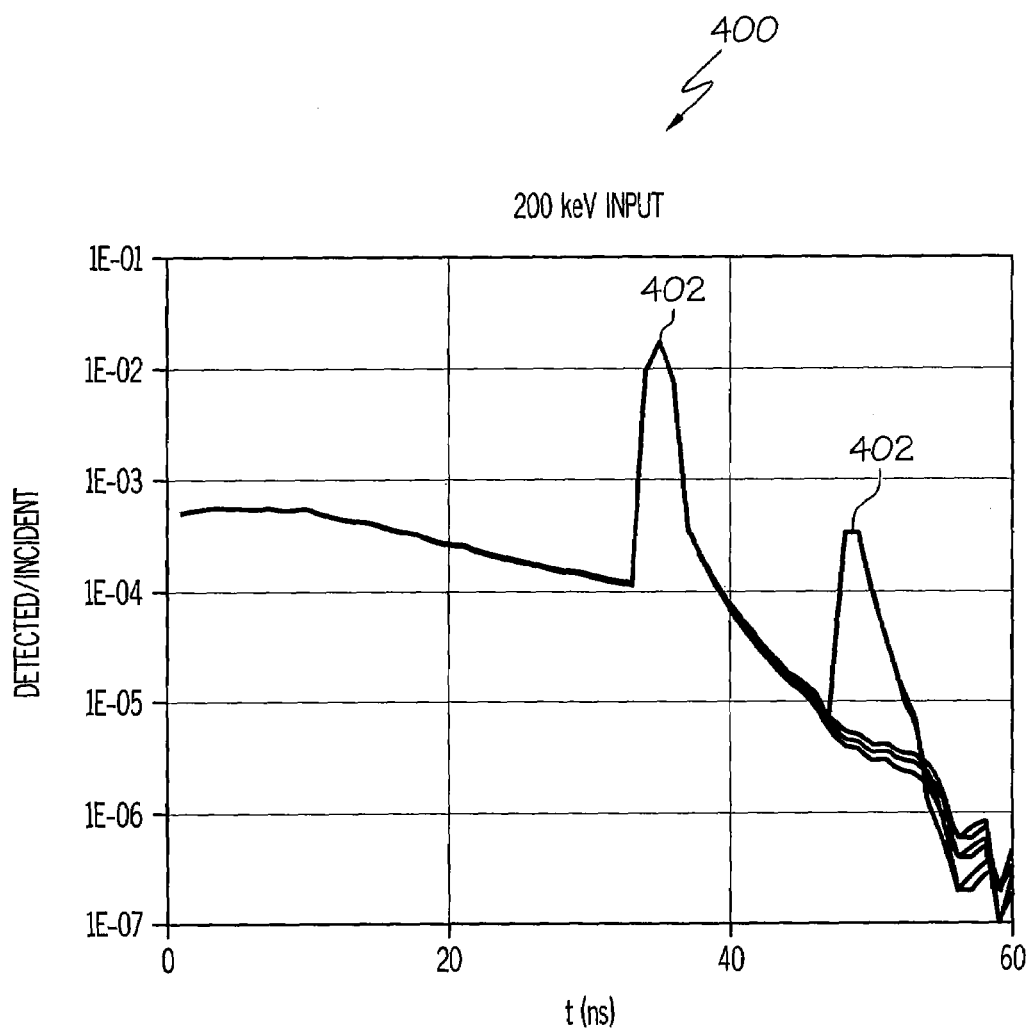
FIG. 4 is an illustration of an exemplary time-resolved data plot used with position information to generate an interior image by a system or method for imaging in a structure in accordance with an embodiment of the present invention.

In block 310, a representation or image of any detected or identified object may be presented to a user or operator. As described with respect to System 100 in FIG. 1A and the system 200 in FIG. 2, the representation or image may be presented on a display, such as display 125 (FIG. 1B) or display 230 (FIG. 2). Referring also to FIG. 4, FIG. 4 is an illustration of an exemplary time-resolved data plot 400 generable by a system, such as system 100, 200 or a similar system, or method, such as method 300 or a similar method for imaging in a structure in accordance with an embodiment of the present invention. The data plot 400 is generated from a time-resolved function similar to the function 126 and illustrates a first peak 402 corresponding to a front wall and a second peak corresponding to the object. Similar to that previously discussed, the energy beam may have a predetermined size in order to provide vertical and horizontal resolution to the image. In another embodiment of the present invention, the energy beam may be scanned to provide a volumetric image of the location of the object of the image in the structure similar to that described with respect to the system 100 of FIG. 1A and the method 300 of FIG. 3.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

What is claimed is:

1. A system for imaging in a structure, comprising:
an energy beam source to direct an energy beam at the structure;
a detector to detect a backscatter of the energy beam from any object in the structure;
a computing device; and
a time-resolved function operating on the computing device to generate a data plot and an image of any object in the structure using the backscatter of the energy beam, wherein the time-resolved function determines a spatial depth of any object based on a time of return of the backscatter of the energy beam.

2. The system of claim 1, wherein the time of return of the backscatter of the energy beam comprises a function of a distance of any object from the energy beam source.

3. The system of claim 1, wherein the detector comprises a time gating feature.

4. The system of claim 1, wherein the energy beam comprises a multiplicity of monoenergetic photons.

5. The system of claim 4, wherein the energy beam further comprises:
a chosen energy;
a predetermined beam size; and
a selected pulse duration.

6. The system of claim 4, wherein the energy beam further comprises:
a predetermined beam size of between about one inch and about twenty feet; and
a selected pulse duration of about twenty picoseconds or less.

7. The system of claim 1, wherein the detector comprises a predetermined time gating sensitivity to detect the backscatter of an energy beam including a pulse duration of about 9-10 picoseconds.

8. The system of claim 1, wherein the energy beam comprises a predetermined beam size to provide a horizontal and vertical resolution of the image of any object.

9. The system of claim 1, wherein the detector comprises a plurality of collimated detectors to provide a horizontal and vertical resolution of the image of any object and the time-resolved function provides a depth resolution.

10. The system of claim 9, wherein the energy beam comprises a predetermined beam size for detection of the backscatter of the energy beam from any object by the plurality of collimated detectors.

11. The system of claim 1, wherein the time-resolved function substantially eliminates any noise so that about 10 to about 100 or more photons backscattered from an energy beam pulse permit detection of any object in the structure.

12. The system of claim 1, further comprising a mechanism to scan the energy beam to create a backscatter volumetric image of a location of any object in the structure.

13. The system of claim 12, wherein the energy beam is scannable in a raster mode.

14. The system of claim 1, further comprising a vehicle, wherein the energy beam source and the detector are mounted to the vehicle for movement of the energy beam source and the detector with respect to the structure.

15. The system of claim 1, further comprising:
a first vehicle, wherein the energy beam source is mounted to the first vehicle for movement of the energy beam source; and
a second vehicle, wherein the detector is mounted to the second vehicle for movement of the detector relative to the structure.

16. The system of claim 1, further comprising a display to present the image including a visualization of an interior of the structure showing a location of any object relative to any other objects and a front wall, a back wall and any interior walls of the structure.

17. A system for imaging in a structure, comprising:
an energy beam source to direct an energy beam at the structure;
a detector to detect a backscatter of the energy beam from any object in the structure;
a computing device;
a time-resolved function operating on the computing device to generate an image of any object in the structure using the backscatter of the energy beam, wherein the time-resolved function includes an element to determine a spatial depth of any object based on a time of return of the backscatter of the energy beam; and
at least one vehicle to move at least one of the energy beam source and the detector relative to the structure.

18. The system of claim 17, wherein the at least one vehicle comprises:
a first vehicle, wherein the energy beam source is mounted to the first vehicle for movement of the energy beam source; and
a second vehicle, wherein the detector is mounted to the second vehicle for movement of the detector relative to the structure.

19. The system of claim 18, wherein the detector comprises a plurality of collimated detectors to provide a horizontal and vertical resolution of the image of any object and the time-resolved function provides a depth resolution.

20. The system of claim 19, wherein the energy beam comprises a predetermined beam size for detection of the backscatter of the energy beam from any object by the plurality of collimated detectors.

21. The system of claim 17, wherein the detector comprises a time gating feature.

22. The system of claim 17, wherein the energy beam comprises a multiplicity of monoenergetic photons.

23. The system of claim 17, wherein the detector comprises a predetermined time gating sensitivity to detect the backscatter of an energy beam including a pulse duration of about 9-10 picoseconds.

24. The system of claim 17, further comprising a mechanism to scan the energy beam to create a backscatter volumetric image of a location of any object in the structure.

25. A method for imaging in a structure, comprising:
directing an energy beam at the structure;
detecting a backscatter of the energy beam from any object in the structure;
determining a spatial depth of any object based on a time of return of the backscatter of the energy beam; and
generating an image of any object in the structure by applying a time-resolved function to the backscatter of the energy beam.

26. The method of claim 25, wherein detecting the backscatter of the energy beam comprises time gating the backscatter of the energy beam to determine a spatial depth of any object in the structure.

27. The method of claim 25, wherein directing the energy beam comprises generating the energy beam with a predetermined pulse duration to permit the backscatter of the energy beam to be detected by the time-resolved function.

28. The method of claim 25, wherein directing the energy beam comprises directing a multiplicity of monoenergetic photons at the structure.

29. The method of claim 28, further comprising detecting backscattered photons of the energy beam using a time gating detector.

30. The method of claim 25, further comprising:
determining a resolution in depth of any object by a time gating sensitivity of a backscatter detector; and
determining a horizontal and a vertical resolution of any object by a beam size of the energy beam.

31. The method of claim 25, further comprising:
determining a resolution in depth of any object by a time gating sensitivity of a backscatter detector; and
determining a horizontal and a vertical resolution of any object by a scheme of a collimated detector.

32. The method of claim 25, further comprising mounting an energy beam source and a detector to detect the backscatter of the energy beam to a vehicle.

33. The method of claim 25, further comprising:
mounting an energy beam source to a first vehicle; and
mounting a detector to detect the backscatter of the energy beam to a second vehicle.

34. A method of imaging in a structure, comprising:
generating an energy beam to provide an energy beam pulse echo from any object in the structure;
determining a spatial depth of any object based on a time of return of the energy beam pulse echo; and
generating an image of any object in the structure from the energy beam pulse echo.

35. The method of claim 34, further comprising:
determining a resolution in depth of any object by a time gating sensitivity of a detector to detect the energy beam pulse echo; and
determining a horizontal and a vertical resolution of any object by a beam size of the energy beam.

36. The method of claim 34, further comprising:
determining a resolution in depth of any object by a time gating sensitivity of a detector to detect the energy beam pulse echo; and
determining a horizontal and a vertical resolution of any object by a scheme of a collimated detector.

37. The method of claim 34, further comprising mounting an energy beam source and a detector to detect the energy beam pulse echo to a vehicle.

38. The method of claim 34, further comprising
mounting an energy beam source to a first vehicle; and
mounting a detector to detect the energy beam pulse echo to a second vehicle.

* * * * *